United States Patent [19]

Notari et al.

[11] Patent Number: 5,780,645
[45] Date of Patent: Jul. 14, 1998

[54] PROCEDURE FOR ALKYLATION OF IMIDES

[75] Inventors: Marcello Notari, Parma; Franco Mizia, S. Donato Milanese; Franco Rivetti, Milan, all of Italy

[73] Assignee: Enichem S.p.A., Milan, Italy

[21] Appl. No.: 775,800

[22] Filed: Dec. 31, 1996

[30] Foreign Application Priority Data

Jan. 19, 1996 [IT] Italy ................... MI96A0079

[51] Int. Cl.$^6$ ............ C07D 207/40; C07D 207/404
[52] U.S. Cl. ............ 548/530; 548/545; 548/546; 548/547
[58] Field of Search ............ 548/530, 545, 548/546, 547

[56] References Cited

FOREIGN PATENT DOCUMENTS 2 533 558  3/1984  France .
1 963 728  9/1970  Germany .
27 26 682  12/1978  Germany .

*Primary Examiner*—José G. Dees
*Assistant Examiner*—Jane C. Osweki
*Attorney, Agent, or Firm*—Oblon, Spivak, McClelland, Maier & Neustadt, P.C.

[57] ABSTRACT

A process for the alkylation of imides wherein the imides are reacted with a dialkyl carbonate, in the liquid state, at a temperature of between 100° C. and 250° C. and at a pressure of between 0 and 60 atmospheres in the presence of a basic catalyst. The dialkyl carbonate reagents are not very toxic and are thermally stable and their use as alkylation agents makes it possible to produce waste products with a negligible saline content.

22 Claims, No Drawings

PROCEDURE FOR ALKYLATION OF IMIDES

This invention relates to a procedure for the alkylation of imides.

In particular it relates to a procedure in which the imides are reacted with a dialkylic ester of carbonic acid.

It is well known that imides are conventionally alkylated by reacting the corresponding alkaline metal salt with alkyl halide, dialkyl sulphate or alkyl tosylate.

For example, potassium phthalimide, a reagent used in the Gabriel synthesis of amines is alkylated using alkyl iodide or bromide in dimethylformamide as the solvent (Sheehan et al., J. Am. Chem. Soc. 72, 2786, 1950; Chem. Int. Ed. Engl. 7, 919–930, 1968), or in toluene but in the presence of a phase transfer catalyst (Soai et al. Chem. Soc. Jpn., 55, 1671, 1982; Landini et al. Synthesis, 389, 1976).

Another example is given by N-N' dialkylimides of the perylenetetra carboxylic acid 3-4-9-10. These imides are obtained through alkylation of the alkaline salt of perylenedi-imide with dialkyl sulphate or an alkyl halide or alkyl tosylate and are used as organic pigments in the dyeing industry.

The patents DE 1963728 and U.S. Pat. No. 3,673,192 contain descriptions of a process in which perylenedi-imide is made to react with an excess of dialkylsulphate at a temperature of 90°–100° C. in the presence of an excess of sodium hydroxide and with ethylene glycol as the solvent.

The patents DE 2727484 and DE 2726682 describe a procedure for alkylation of perylenedi-imide with alkyl halide in an aqueous medium and in the presence of an excess of sodium hydroxide at a temperature of 100° C.

Furthermore, the patent DE 2726682 discloses that the addition of a quaternary ammonium salt to the reaction mixture produces a product with high purity and good pigment properties without further treatment.

In the patent JP 48020007, alkylation of the potassium salt of perylenedi-imide is performed by using toluensulphonated alkyl-p as the alkylation agent, in an aqueous medium.

The problems common to all the imide alkylating procedures described in the literature are that they use extremely toxic alkylating agents and they produce by-products with a high saline content.

For example dimethylsulphate is highly toxic both when inhaled or absorbed; the $LD_{50}$ for a rat is 440 mg/Kg and its use also causes the production of sodium or potassium sulphate in quantities stoichiometric to the N-methylimide which it is wished to produce. In order to prevent pollution, this makes subsequent treatment of the waste water necessary with a consequent increase in production costs.

Methyl chloride and bromide present the same problems. These are in fact gases that exert a toxic action on the central nervous system; the $LD_{50}$ of methyl bromide for mice is 200 mg/Kg and the gases produce sodium and potassium halides as by-products.

Methyl tosylate is not only toxic, it is also an extremely unstable reagent.

A procedure for the alkylation of imides has now been found that overcomes these well-known problems since it uses dialkyl carbonates as alkylating agents, not very toxic and thermally stable reagents.

Furthermore, the use of this procedure produces by-products with a negligible saline content. In fact alkylation using dialkyl carbonate produces alkylic alcohol and carbon dioxide as by-products.

This invention therefore consists of a procedure for the alkylation of imides characterised by the fact that the imides in formula I are reacted with a dialkyl carbonate of formula II, in the liquid phase, at a temperature of between 100° C. and 250° C. and at a pressure of between 0 and 60 atmospheres in the presence of a basic catalyst and optionally a quaternary ammonium salt according to the equation:

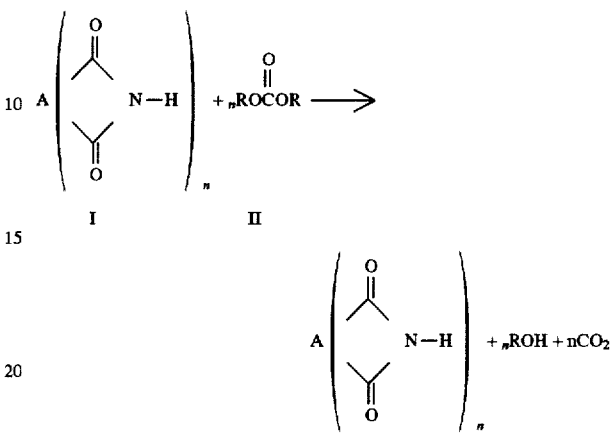

in which R is a monovalent organic radical; A is an organic radical containing up to 30 carbon atoms which may additionally contain oxygen, nitrogen and sulphur atoms and halogens; the imide of formula I can be cyclic or acyclic: when it is cyclic n is equal to 1 or 2 and A is a either a bivalent or tetravalent organic radical; when it is acyclic, n is equal to 1 and A consists of two monovalent organic radicals.

More precisely the above radical R can be: an alkyl radical that contains from 1 to 16 carbon atoms and preferably from 1 to 4 carbon atoms; an arylalkyl radical that contains from 7 to 20 carbon atoms such as for example the benzyl radical; a cycloalkyl radical that contains from 5 to 10 carbons atoms such as the cyclohexyl radical; an alpha beta saturated alkene radical that contains from 3 to 6 carbon atoms such as the allyl radical.

The organic carbonates preferred for the alkylation of imides are dimethyl and diethyl carbonate with greater preference being given to dimethyl carbonate.

Examples of the above mentioned bivalent organic radicals include linear or branched alkylene radicals usually containing from 1 to 8 carbon atoms; arylene radicals, homocyclic or heterocyclic, monocyclic or polycyclic, usually containing from 6 to 30 carbon atoms.

Examples of tetravalent radicals include the radicals derived from polycyclic, homocyclic or heterocyclic hydrocarbons usually containing up to 30 carbon atoms such as the perylene radical for example.

When the imide is acyclic, it has formula III where A consists of two monovalent radicals R1 and R2 either the same or different.

Examples of the above mentioned monovalent organic radicals include: linear or branched alkyl radicals, usually containing from 1 to 10 carbon atoms; linear branched alkylene radicals, usually containing from 1 to 10 carbon atoms; homocyclic or heterocyclic, monocyclic or polycyclic aryl radicals, usually containing from 6 to 30 carbon atoms; arylalkyl radicals, usually containing from 7 to 20 carbon atoms and cycloalkyl radicals that contain from 5 to 10 carbon atoms.

The reaction of the imide with dialkyl carbonate is usually carried out in the liquid state.

It can be carried out in the presence of an inert solvent that is capable of increasing the solubility of the imide and of the catalyst in the reaction mixture or the dialkylcarbonate itself can act as the reaction solvent.

The molar ratio between the dialkylcarbonate and the initial imide for the imide groups present can vary in the 1.1:1 to 100:1 range, but preferably in the 2:1 to 50:1 range.

Examples of suitable solvents include the alcohols, dimethylformamide, dimethylsulpho-oxide, acetonitrile, benzonitrile, dioxan, tetrahydro furan and chlorine containing solvents such as methyl chloride, chloroform and chlorobenzene.

When the solvent is an alcohol it is preferable to use the alcohol corresponding to the radical R present in the carbonate that is employed.

However, considering the toxicity of the various solvents and the extent to which N-methylimides and the catalyst are soluble in them, the alcohol solvents, dimethylformamide, acetonitrile and dioxan are those that are preferred.

The quantity of inert solvent used is variable.

Generally there must be sufficient solvent to dissolve the imide at the reaction temperature.

The ratio by weight of the solvent, when used, to the initial quantity of imide can vary within the 0.5:1 to 50:1 range, but preferably in the 1:1 to 10:1 range.

The temperature at which the reaction is carried out can vary in the 100° C. to 250° C. range. The preferred temperature is in the 140° C. to 200° C. range.

The pressure at which the reaction is carried out can vary within a wide range which will also be a function of the operational procedure employed.

Generally pressures equal to or greater than atmospheric pressure are employed within a 0 to 60 atmosphere range. Frequently the self-generated pressure is used.

The reaction is carried out in the presence of a basic catalyst.

Examples of catalysts that can be used include alkali metal or alkaline earth compounds that are basic such as carbonates, oxides, hydroxides, alkoxides or basic nitrogen compounds such as triethylamine.

The preferred catalyst is potassium carbonate.

The molar ratio of the catalyst to the initial imidic nitrogen normally varies in the 0.005:1 to 0.2:1 range and is preferably in the 0.01:1 to 0.1:1 range.

The reaction can be carried out in the presence of a quaternary ammonium salt, as a promoter, although in many cases the presence of this is not indispensable.

Examples of quaternary ammonium salts that may be employed include those that contain the same or different organic radicals directly bound to the nitrogen. These organic radicals can be: alkyl radicals containing from 1 to 18 carbon atoms; arylalkyl radicals containing 7 to 20 carbon atoms such as the benzyl radical; aryl radicals containing from 6 to 10 carbon atoms such as the phenyl radical.

These salts are usually in the form of halides or carbonates.

The ammonium salts generally preferred are: trimethylcetylammonium bromide, trimethylcetylammonium chloride, trimethylbenzylammonium chloride, hexadecytrimethylammonium chloride.

The molar ratio of the quaternary ammonium salt to the initial imidic nitrogen normally varies in the 0.005:1 to 0.2:1 range and is preferably in the 0.01:1 to 0.1:1 range.

When the reaction is complete the excess dialkylcarbonate, the alcohol by-product and the inert solvent are recovered the methylated imide is isolated and purified using conventional methods such as extraction, distillation and crystallisation.

The examples reported below are purely illustrative and are not intended as limits to this invention.

In these examples the alkylation reaction is carried out in a stainless steel autoclave equipped with a magnetic stirrer, a manometer and a valved sampling device. It is heated for immersion in an oil bath.

Example 1

A stainless steel autoclave with a capacity of 250 ml, equipped as described above, is loaded with 15 g of phthalimide, 92.5 g of dimethylcarbonate, 33 g. of methanol and 0.35 g of potassium carbonate. The stirrer is switched on and the autoclave is heated with a thermostatic oil bath until the temperature inside the reactor reaches 170° C. As the reaction proceeds, $CO_2$ is produced and the internal pressure builds up to a maximum value of 25.5 atmospheres. After approximately one hour of reaction at a temperature of 170° C., more than 99% of the phthalimide is converted and the selectivity in N-methyl phthalimide is total. The autoclave is allowed to cool to environmental temperature, the mixture is transferred to a flask and the methanol that has formed is recovered together with the excess dimethyl carbonate for distillation at atmospheric pressure. The residue is taken with 250 ml of dimethylcarbonate and is filtered to eliminate the catalyst. The solvent is taken away for distillation and 16.4 g of N-methyl phthalimide is obtained (yield=99%).

Example 2

A stainless steel autoclave with a capacity of 250 ml, equipped as described above, is loaded with 11 g of succinimide, 100 g. of dimethylcarbonate, 35.5 g. of methanol and 0.38 g of potassium carbonate. The stirrer is switched on and the autoclave is heated until the temperature inside the reactor reaches 170° C. During the reaction, $CO_2$ is produced and the internal pressure of the reactor builds up to a maximum value of 25 atmospheres. After approximately 50 minutes of reaction at a temperature of 170° C., 99.5% of the phthalimide has been converted and the selectivity in N-methyl phthalimide is 95%. Once the reaction period has finished the autoclave is allowed to cool to environmental temperature, and the methanol and the dimethyl carbonate is taken away for distillation. The residue is taken with 60 ml of dimethylcarbonate and is filtered to eliminate the catalyst. The solvent is eliminated for distillation and 12.5 g of N-methyl succinimide is obtained with a gaschromatography strength of 94% which is purified for recrystallisation by a chloroform-hexane mixture.

Example 3

A stainless steel autoclave with a capacity of 100 ml, equipped as described above, is loaded with 5.4 g of the di-imide of the tetracarboxyl perylene acid 3,4,9,10, with 25 g. of dimethylcarbonate, 20 g. of N—N dimethylformamide, 0.27 g. of trimethylcetylammonium chloride and 0.21 g. of potassium carbonate. The stirrer is switched on and the autoclave is heated with a thermostatic oil bath until the temperature inside the reactor reaches 170° C. As the reaction proceeds, carbon dioxide is produced and the internal pressure of the reactor builds up to a maximum value of 18 atmospheres. After 7 hours of reaction the autoclave is allowed to cool to environmental temperature, the mixture is transferred to a flask and the methanol and dimethylcarbonate is removed at 110° C. for distillation at atmospheric pressure. Afterwards, when the internal pressure has fallen the dimethylformamide is removed for distillation. The residue is suspended in 100 ml of distilled water, filtered, washed with two 50 ml portions of distilled water and dried at a temperature of 100° C.

After drying, 5.4 g. of N-N'-dimethylimide of the tetracarboxyl perylene acid 3,4,9,10 is obtained. The purity of the product was checked using DRIFT-FT IR and $^{13}$C-CP-MAS-NMR techniques for comparison with a product in commerce of known purity.

Example 4

A stainless steel autoclave with a capacity of 250 ml, equipped as described above, is loaded with 12 g of phthalimide, 58 g of diethyl carbonate, 84 g. of N—N dimethylformamide and 0.284 g of potassium carbonate. The stirrer is switched on and the autoclave is heated with a thermostatic oil bath until the temperature inside the reactor reaches 200° C. As the reaction proceeds, carbon dioxide is produced and the internal pressure builds up to a maximum value of 15 atmospheres. After approximately two hours of reaction at a temperature of 200° C. more than 99% of the phthalimide has been converted, the N-ethylphthalimide yield is 98% and the selectivity in N-ethyl phthalimide is greater than 99%. Once the reaction period is complete the autoclave is allowed to cool to environmental temperature and the ethanol, the diethylcarbonate and the dimethylformamide is removed for distillation at reduced pressure. The residue is dissolved in 150 ml of methyl chloride, washed with distilled water, dried on sodium sulphate and filtered. Thirteen grams of N-ethyl phthalimide is obtained by evaporation of the solvent and it can be further purified through crystallisation by a mixture of chloroform-hexane.

We claim:

1. A process for the alkylation of imides comprising reacting imides of formula I with a dialkyl carbonate of formula II, in the liquid state, at a temperature of between 100° C. and 250° C. and at a pressure of between 0 to 60 atmospheres in the presence of a basic catalyst according to the equation:

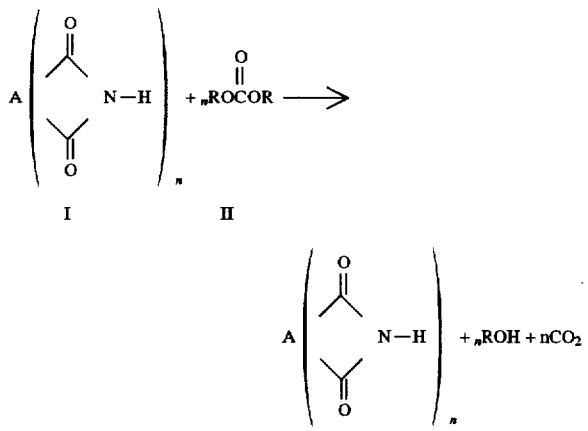

in which R is an alkyl radical; A is an organic radical, containing up to 30 carbon atoms, and which may also contain oxygen, nitrogen and sulphur atoms and halogens; the imide of formula I can be cyclic or acyclic: when it is cyclic, n is equal to 1 or 2 and A is a bivalent or tetravalent organic radical; when it is acyclic n is equal to 1 and A consists of two monovalent organic radicals.

2. A process according to claim 1 wherein the dialkyl carbonate of formula II is dimethylcarbonate or diethyl carbonate.

3. A process according to claim 1 or 2 wherein the dialkylcarbonate of formula II is reacted with the imide in formula I in a molar ratio within the 1.1:1 to 100:1 range with reference to the imidic groups present.

4. A process according to claim 1 wherein the reaction is carried out at a temperature of between 140° C. and 200° C.

5. A process according to claim 1 wherein the catalyst is potassium carbonate.

6. A process according to claim 1 wherein the molar ratio of the catalyst to the initial imidic nitrogen falls within the 0.005:1 to 0.2:1 range.

7. A process according to claim 1 wherein the reaction is carried out in the presence of a quaternary ammonium salt.

8. A process according to claim 7 wherein the quaternary ammonium salt is trimethylcetylamnmonium bromide.

9. A process according to claim 7 or 8 wherein the molar ratio of the quaternary ammonium salt to the initial imidic nitrogen falls within the 0.005:1 to 0.2:1 range.

10. A process according to claim 1 wherein the reaction is carried out in the presence of a solvent.

11. Procedure according to claim 10 wherein the solvent is dimethylformamide or methanol.

12. Procedure according to claim 10 or 11 wherein the ratio by weight of the solvent to the initial imide falls within the 0.5:1 to 50:1 range.

13. A process according to claim 2 wherein the dialkylcarbonate of formula II is reacted with the imide in formula I in a molar ratio in the 2:1 to 50:1 range with reference to the imidic groups present.

14. A process according to claim 2 wherein the reaction is carried out at a temperature of between 140° C. and 200° C.

15. A process according to claim 2 wherein the catalyst is potassium carbonate.

16. A process according to claim 2 wherein the molar ratio of the catalyst to the initial imidic nitrogen falls within the 0.01:1 to 0.1:1 range.

17. A process according to claim 2 wherein the reaction is carried out in the presence of a quaternary ammonium salt.

18. A process according to claim 2 wherein the quaternary ammonium salt is trimethylcetylammonium bromide.

19. A process according to claim 7 or 8 wherein molar ratio of the quaternary ammonium salt to the initial imidic nitrogen falls within the 0.01:1 to 0.1:1 range.

20. A process according to claim 2 wherein the reaction is carried out in the presence of a solvent.

21. A process according to claim 20 wherein the solvent is dimethylformamide or methanol.

22. A process according to claim 20 or 21 wherein the ratio by weight of the solvent to the initial imide falls within the 1:1 to 10:1 range.

* * * * *